(12) United States Patent
Inoue

(10) Patent No.: US 10,495,789 B2
(45) Date of Patent: Dec. 3, 2019

(54) ILLUMINATION LENS AND ILLUMINATION OPTICAL SYSTEM FOR AN ENDOSCOPE

(71) Applicant: FUJIFILM Corporation, Tokyo (JP)

(72) Inventor: Kazuki Inoue, Saitama (JP)

(73) Assignee: FUJIFILM Corporation, Tokyo (JP)

(*) Notice: Subject to any disclaimer, the term of this patent is extended or adjusted under 35 U.S.C. 154(b) by 43 days.

(21) Appl. No.: 15/962,692

(22) Filed: Apr. 25, 2018

(65) Prior Publication Data
US 2018/0310814 A1 Nov. 1, 2018

(30) Foreign Application Priority Data

Apr. 28, 2017 (JP) ................... 2017-090789

(51) Int. Cl.
| | | |
|---|---|---|
| *G02B 3/02* | (2006.01) | |
| *A61B 1/06* | (2006.01) | |
| *G02B 19/00* | (2006.01) | |
| *A61B 1/00* | (2006.01) | |
| *G02B 23/24* | (2006.01) | |
| *A61B 1/07* | (2006.01) | |

(52) U.S. Cl.
CPC ............ *G02B 3/02* (2013.01); *A61B 1/00096* (2013.01); *A61B 1/0623* (2013.01); *G02B 19/0009* (2013.01); *G02B 19/0014* (2013.01); *G02B 23/2469* (2013.01); *A61B 1/07* (2013.01)

(58) Field of Classification Search
None
See application file for complete search history.

(56) References Cited

FOREIGN PATENT DOCUMENTS

| | | |
|---|---|---|
| JP | 5269530 B2 | 8/2013 |
| JP | 2013-246255 A | 12/2013 |

*Primary Examiner* — Darryl J Collins
(74) *Attorney, Agent, or Firm* — Sughrue Mion, PLLC

(57) ABSTRACT

An illumination lens is formed of one lens, and an aspherical surface is formed on an incident surface on which light generated from a light source is to be incident so that the incident surface has a convex shape in a paraxial region. In a case in which the amount of sag at each point on an aspherical surface corresponding to a height from an optical axis is expressed by a function of h, predetermined Conditional Expression, which is related to a height at which a second derivative of the function with respect to h is 0 and the maximum height of the aspherical surface, is satisfied. Predetermined Conditional Expression related to a refractive index of the illumination lens is satisfied.

14 Claims, 4 Drawing Sheets

EXAMPLE 1

EXAMPLE 2

EXAMPLE 3

ILLUMINATION LENS AND ILLUMINATION OPTICAL SYSTEM FOR AN ENDOSCOPE

CROSS-REFERENCE TO RELATED APPLICATIONS

The present application claims priority under 35 U.S.C. § 119 to Japanese Patent Application No. 2017-090789, filed on Apr. 28, 2017. The above application is hereby expressly incorporated by reference, in its entirety, into the present application.

BACKGROUND OF THE INVENTION

1. Field of the Invention

The present invention relates to an illumination lens that can be applied to an illumination device of an endoscope or the like, and an illumination optical system for an endoscope that includes the illumination lens.

2. Description of the Related Art

In the past, lenses disclosed JP5269530B and JP2013-246255A to be described below have been known as a lens used in an illumination device. JP5269530B discloses a lens that can be applied to an illumination device of an endoscope, is combined with a fiber bundle guiding light generated from a light source at the time of use, converges a part of incidence rays inside the lens, and then emits the converged light as divergent light. JP2013-246255A discloses a collimating lens that can be applied to an illumination device of a microscope and collimates light generated from a light source.

SUMMARY OF THE INVENTION

As the angle of an observation optical system of an endoscope is widen, the angle of an illumination optical system of an endoscope is required to be widened. Since high energy is generated at the convergence point of light in the case of a certain design specification in an optical system that converges light generated from a light source and then emits the converged light as divergent light to obtain wide-angle illumination light, it is necessary to be careful so that light does not invade an object to be observed. Particularly, low-invasive light is desired in a medical endoscope to reduce a patient's burden. Further, the illumination optical system of an endoscope is required to have wide-angle light distribution characteristics in which the quantity of light is secured even in the peripheral portion of an illumination field. Furthermore, since various observation methods using light having various wavelengths have been proposed in recent years, an illumination optical system, which is less changed depending on a wavelength, is required.

It is desired that the lens system disclosed in JP5269530B is much less changed depending on a wavelength in comparison with the recent demand. It is difficult for the lens system disclosed in JP2013-246255A to secure the quantity of light in the peripheral portion of an illumination field in a case in which the lens system tries to realize wide-angle light distribution characteristics.

The invention has been made in consideration of the above-mentioned circumstances, and an object of the invention is to provide an illumination lens that has wide-angle light distribution characteristics in which the quantity of light is secured even in the peripheral portion of an illumination field, is less changed depending on a wavelength, and can obtain low-invasive illumination light, and an illumination optical system for an endoscope including the illumination lens.

An illumination lens of the invention is an illumination lens that is used in an illumination optical system for an endoscope. The illumination lens consists of one lens. An aspherical surface is formed on an incident surface on which light generated from a light source is to be incident so that the incident surface has a convex shape in a paraxial region. The aspherical surface has at least one hs satisfying the following Conditional Expression (1) in a case in which a height from an optical axis is denoted by h, the amount of sag at each point on the aspherical surface corresponding to the height h is expressed by Sag(h) as a function of h, a height at which a second derivative of Sag(h) with respect to h is 0 is denoted by hs, and a maximum height of the aspherical surface from the optical axis is denoted by hmax.

$$0 < hs/h\max < 0.5 \tag{1}$$

The following Conditional Expression (2) is satisfied in a case in which a refractive index of the illumination lens with respect to a line d is denoted by Nd.

$$1.79 < Nd < 2 \tag{2}$$

In the illumination lens of the invention, it is preferable that the aspherical surface has at least one hs satisfying the following Conditional Expression (1-1).

$$0 < hs/h\max < 0.49 \tag{1-1}$$

Further, in the illumination lens of the invention, it is preferable that the following Conditional Expression (2-1) is satisfied.

$$1.8 < Nd < 2 \tag{2-1}$$

Furthermore, in the illumination lens of the invention, in a case in which Abbe's number of the illumination lens based on the line d is denoted by $\nu d$, it is preferable that the following Conditional Expression (3) is satisfied and it is more preferable that the following Conditional Expression (3-1) is satisfied.

$$34.5 < \nu d < 47.5 \tag{3}$$

$$34.75 < \nu d < 47.25 \tag{3-1}$$

Moreover, in the illumination lens of the invention, it is preferable that an emission surface from which the light incident from the incident surface is to be emitted is a flat surface.

Further, in the illumination lens of the invention, it is preferable that an intersection of a ray incident on the incident surface in parallel to the optical axis at a height of 0.1×hmax and a ray incident on the incident surface in parallel to the optical axis at a height of 0.4×hmax is positioned inside the illumination lens. In this case, it is preferable that the intersection is positioned closer to the light source than a middle point of a thickness of the illumination lens, which is positioned on the optical axis, in a direction of the optical axis.

Furthermore, in the illumination lens of the invention, in a case in which a distance between an intersection of a ray incident on the incident surface in parallel to the optical axis and the incident surface and an intersection of an extension line of refracted light of the ray from the incident surface and the optical axis in the direction of the optical axis is denoted by fd and a thickness of the illumination lens along the optical axis is denoted by t, it is preferable that at least a part of rays, which are incident on the incident surface in parallel to the optical axis at a height ha in a range of "0.1× hmax≤ha≤0.5×hmax", satisfy the following Conditional Expression (4) and it is more preferable that at least a part of the rays satisfy the following Conditional Expression (4-1).

$$0.1 < fd/t < 1 \quad (4)$$

$$0.15 < fd/t < 0.95 \quad (4\text{-}1)$$

Moreover, in the illumination lens of the invention, in a case in which a distance between an surface apex of the incident surface and an intersection of an extension line of refracted light of a ray from the incident surface and the optical axis in the direction of the optical axis, in a case in which the ray is incident on the incident surface in parallel to the optical axis at a height of 0.4×hmax, is denoted by D4 and a distance between the surface apex of the incident surface and an intersection of an extension line of refracted light of a ray from the incident surface and the optical axis in the direction of the optical axis, in a case in which the ray is incident on the incident surface in parallel to the optical axis at a height of 0.8×hmax, is denoted by D8, it is preferable that the following Conditional Expression (5) is satisfied and it is more preferable that the following Conditional Expression (5-1) is satisfied.

$$1.8 < (D4-D8)/h\text{max} < 2.5 \quad (5)$$

$$1.85 < (D4-D8)/h\text{max} < 2.45 \quad (5\text{-}1)$$

Further, in the illumination lens of the invention, it is preferable that the aspherical surface has only one hs in a range of "0<h≤hmax" in a cross section including the optical axis.

An illumination optical system for an endoscope of the invention comprises the illumination lens of the invention.

"consist(s) of" in this specification may intend to include a lens that does not substantially have a power; optical elements other than a lens, such as a diaphragm, a filter, and a cover glass; a lens flange; a lens barrel; and the like other than elements serving as components.

According to the invention, it is possible to provide an illumination lens that has wide-angle light distribution characteristics in which the quantity of light is secured even in the peripheral portion of an illumination field, is less changed depending on a wavelength, and can obtain low-invasive illumination light, and an illumination optical system for an endoscope including the illumination lens.

DESCRIPTION OF THE PREFERRED EMBODIMENTS

Figure 1:
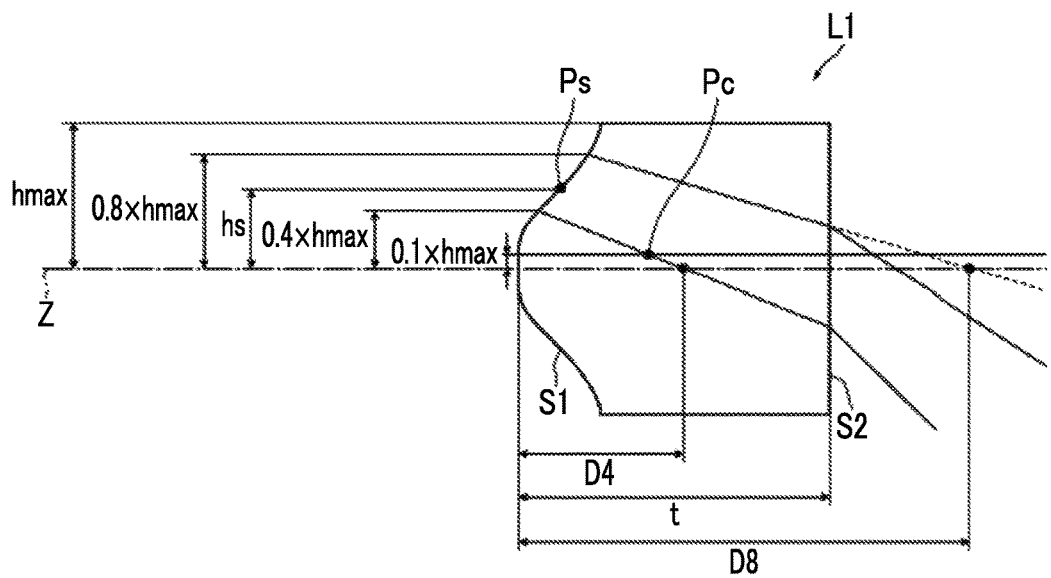
FIG. 1 is a cross-sectional view showing the structure of an illumination lens according to an embodiment of the invention.
Figure 2:
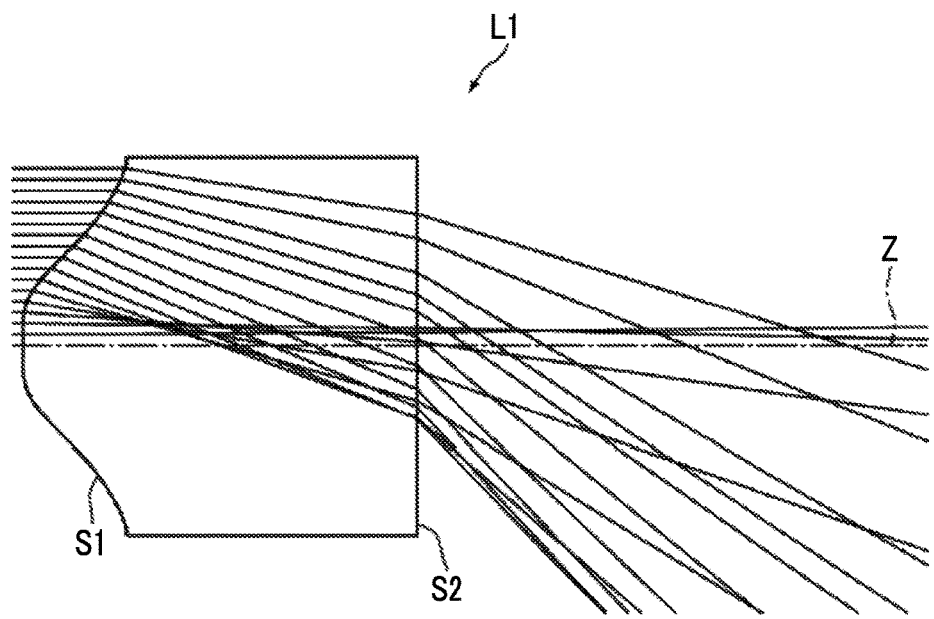
FIG. 2 is a cross-sectional view showing the structure of an illumination lens of Example 1 of the invention and optical paths.

An embodiment of the invention will be described in detail below with reference to the drawings. FIG. 1 is a cross-sectional view showing the structure of an illumination lens L1 according to an embodiment of the invention. FIG. 2 is a diagram showing the structure and optical paths of the illumination lens L1 in a case in which rays are incident on the illumination lens L1 in parallel to an optical axis Z. An example of the structure shown in FIGS. 1 and 2 corresponds to the illumination lens L1 of Example 1 to be described later.

The illumination lens L1 of this embodiment consists of one lens that has a positive refractive power in a paraxial region. The illumination lens L1 is used in an illumination optical system for an endoscope. Light generated from a light source is incident on the illumination lens L1, and the illumination lens L1 emits illumination light to an object to be observed (hereinafter, referred to as an object). FIGS. 1 and 2 are cross-sectional views including the optical axis Z, and a left side in the plane of FIGS. 1 and 2 is shown as a light source side and a right side in the plane of FIGS. 1 and 2 is shown as an object side. The lens surface of the illumination lens L1 corresponding to the light source side is an incident surface S1 on which light generated from the light source is to be incident, and the lens surface of the illumination lens L1 corresponding to the object side is an emission surface S2 from which the light incident from the incident surface S1 is to be emitted.

It is preferable that the emission surface S2 is a flat surface. Since the illumination lens L1 is disposed at the distal end of an insertion part of the endoscope in a case in which the illumination lens L1 is to be mounted on an insertable endoscope, there is a concern that the emission surface S2 may be exposed to body fluid, a cleaning solution, oil and fat, and the like. For this reason, in a case in which the emission surface S2 is a flat surface, it is difficult for the liquid, oil and fat, and the like to adhere to the emission surface S2 and the liquid, oil and fat, and the like easily come off even though the liquid, oil and fat, and the like adhere to the emission surface S2. Accordingly, it is easy to clean the emission surface S2.

An aspherical surface is formed on the incident surface S1 so that the incident surface S1 has a convex shape in a paraxial region. Since the incident surface S1 is formed in this shape, the illumination lens is advantageous in having wide-angle light distribution characteristics in which the quantity of light is secured even in the peripheral portion of an illumination field and in obtaining low-invasive illumination light.

The shape of the aspherical surface of the incident surface S1 will be described below with reference to FIG. 1 that is a cross-sectional view including the optical axis Z, and the like. The aspherical surface of the incident surface S1 is formed so as to have at least one hs satisfying the following Conditional Expression (1) in a case in which a height from the optical axis Z is denoted by h, the amount of sag at each point on the aspherical surface corresponding to the height h is expressed by Sag(h) as a function of h, a height at which the second derivative of Sag(h) with respect to h is 0 is denoted by hs, and the maximum height of the aspherical surface from the optical axis Z is denoted by hmax. In a case in which the aspherical surface of the incident surface S1 is formed as described above, the gradient of the peripheral portion of the incident surface S1 is small so that the aspherical surface has a smooth shape and a difference in the angle of refraction of light for every wavelength is reduced. Accordingly, a change depending on a wavelength can be suppressed even in the case of wide-angle light distribution. Since an endoscope uses light having various wavelengths depending on observation methods, it is preferable that a change caused by a color, that is, a color shift is less. Accordingly, the above-mentioned structure is effective. In a case in which the aspherical surface of the incident surface S1 is formed so as to have at least one hs satisfying the following Conditional Expression (1-1), better characteristics can be obtained.

$$0 < hs/h\max < 0.5 \qquad (1)$$

$$0 < hs/h\max < 0.49 \qquad (1\text{-}1)$$

Here, the amount of sag at each point is displacement from a vertical plane, which meets the surface apex of the incident surface S1 and is perpendicular to the optical axis Z, to each point on the aspherical surface in the direction of the optical axis. Sag(h) can be expressed by, for example, an aspheric equation to be described later.

It is preferable that the aspherical surface of the incident surface S1 has only one hs in the range of "0<h≤hmax" in the cross section including the optical axis Z. In this case, a lens having good manufacturability can be obtained. In FIG. 1, a point on the incident surface S1 corresponding to a height hs above the optical axis Z is shown as a point Ps.

The illumination lens L1 is formed so as to satisfy the following Conditional Expression (2) in a case in which the refractive index of the illumination lens L1 with respect to a line d is denoted by Nd. In a case in which Nd is set so as not to be equal to or lower than the lower limit of the Conditional Expression (2), a large emission angle can be ensured. Accordingly, the illumination lens L1 can have wide-angle light distribution characteristics. Further, the illumination lens L1 is advantageous in securing the quantity of light even in the peripheral portion of an illumination field. In a case in which Nd is set so as not to be equal to or higher than the upper limit of the Conditional Expression (2), a suitable material can be selected from existing optical materials to suppress chromatic aberration. In a case in which the illumination lens L1 is formed so as to satisfy the following Conditional Expression (2-1), better characteristics can be obtained.

$$1.79 < Nd < 2 \qquad (2)$$

$$1.8 < Nd < 2 \qquad (2\text{-}1)$$

Further, it is preferable that the illumination lens L1 is formed so as to satisfy the following Conditional Expression (3) in a case in which Abbe's number of the illumination lens L1 based on the line d is denoted by υd. In a case in which υd is set so as not to be equal to or lower than the lower limit of Conditional Expression (3), chromatic aberration can be suppressed. In a case in which υd is set so as not to be equal to or higher than the upper limit of Conditional Expression (3), a suitable material can be selected from existing optical materials to ensure the refractive power of the illumination lens L1. Accordingly, emitted light can be emitted at a suitable angle. In a case in which the illumination lens L1 is formed so as to satisfy the following Conditional Expression (3-1), better characteristics can be obtained.

$$34.5 < υd < 47.5 \qquad (3)$$

$$34.75 < υd < 47.25 \qquad (3\text{-}1)$$

Furthermore, it is preferable that the illumination lens L1 is formed so that an intersection Pc of a ray incident on the incident surface S1 in parallel to the optical axis Z at a height of 0.1×hmax and a ray incident on the incident surface S1 in parallel to the optical axis Z at a height of 0.4×hmax is positioned inside the illumination lens L1. Luminous flux converged inside the illumination lens L1 is emitted to the outside of the illumination lens L1 as divergent light As understood from FIG. 2, and it is said that this light is not likely to invade an object is low. Since light density is high in a region close to the optical axis Z, high energy is likely to be generated in the region close to the optical axis. However, in a case in which the intersection Pc is positioned inside the illumination lens L1, it is easy that luminous flux close to the optical axis Z is converged inside the illumination lens L1 once and is then diverged and emitted to the outside of the illumination lens L1. Accordingly, the light density outside the lens can be lowered and light can be changed to low-invasive light. Further, since luminous flux is converged inside the illumination lens L1 once and is then emitted to the outside of the illumination lens L1 as divergent light, a range of a wide angle, for example, 140° or more in the entire angle can be illuminated. Particularly, an angle is effectively given to rays, which are close to the optical axis and of which the quantity of light is likely to be increased.

It is preferable that the intersection Pc is positioned closer to the light source than the middle point of the thickness of the illumination lens L1, which is positioned on the optical axis, in the direction of the optical axis. That is, in a case in which the thickness of the illumination lens L1 along the optical axis is denoted by t, it is preferable that the position of the intersection Pc in the direction of the optical axis is present in the range of a distance t/2 toward the object side from the surface apex of the incident surface S1 of the illumination lens L1. In this case, since it is easy to make the intersection Pc be present inside the illumination lens L1 even though there is a variation caused by manufacturing tolerance, it is possible to improve robustness in changing light to low-invasive light. Further, since diffracted light caused by scratches can be relatively suppressed even though scratches or the like are present on the emission surface S2, the unevenness of illumination light can be reduced.

Figure 3A:
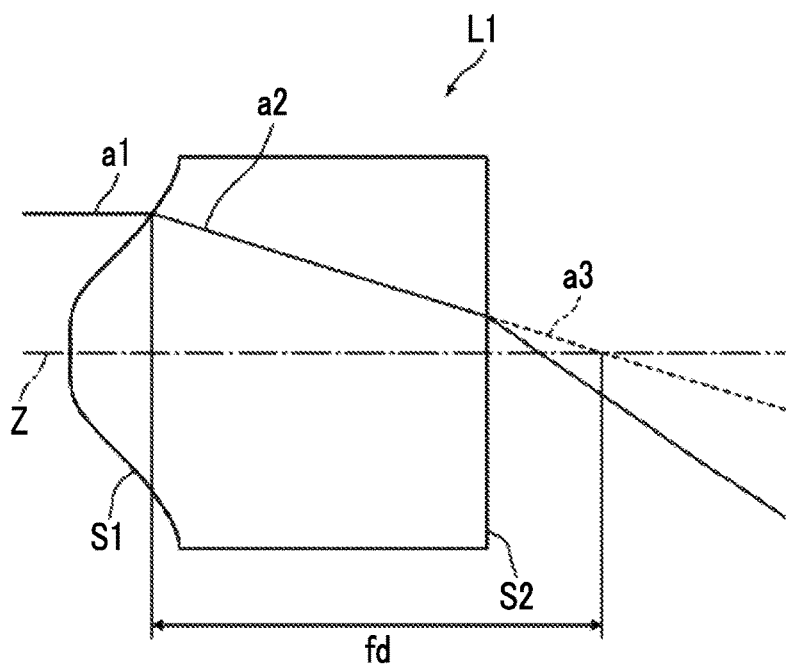
FIG. 3A is a cross-sectional view illustrating a distance fd.
Figure 3B:
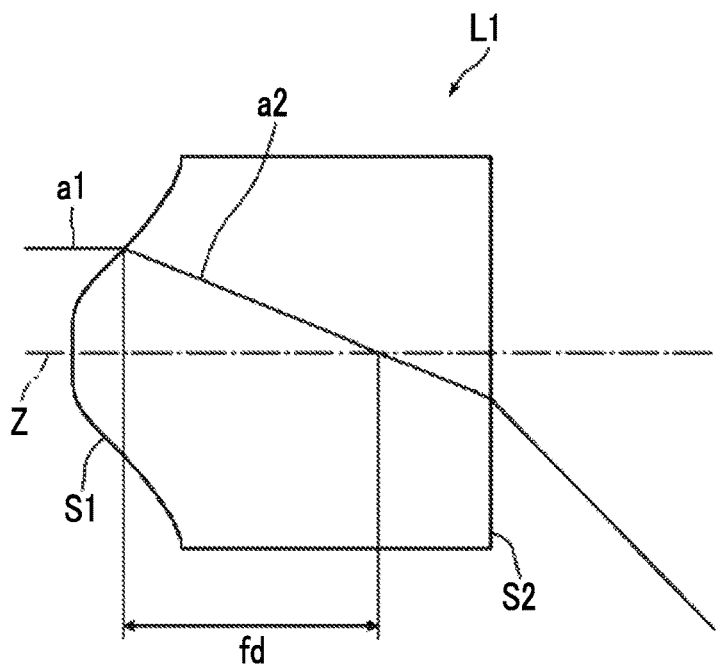
FIG. 3B is a cross-sectional view illustrating a distance fd.

Next, description will be made with reference to FIGS. 3A and 3B. In a case in which a ray a1 parallel to the optical axis is incident on the incident surface S1, a distance between an intersection of the ray a1 and the incident surface S1 and an intersection of an extension line a3 of refracted light a2 of the ray a1 from the incident surface S1 and the optical axis Z in the direction of the optical axis is denoted by fd. The extension line a3 is not an extension line of refracted light from the emission surface S2 and is an extension line of the refracted light a2 from the incident surface S1. FIG. 3A shows an example of a case in which an intersection of the extension line a3 of the refracted light a2 and the optical axis Z is positioned outside the illumination lens L1. FIG. 3B shows an example of a case in which an intersection of the extension line of the refracted light a2 and the optical axis Z is positioned inside the illumination lens L1.

It is preferable that the illumination lens L1 is formed so that at least a part of rays, which are incident on the incident surface S1 in parallel to the optical axis at a height ha in a range of "0.1×hmax≤ha≤0.5×hmax", satisfy the following Conditional Expression (4) related to the distance fd and the thickness t of the illumination lens L1 along the optical axis having been defined above. In a case in which fd is set so as not to be equal to or lower than the lower limit of Conditional Expression (4), a force for bending a ray is not excessively increased. Accordingly, even though there is a variation caused by manufacturing tolerance, an influence of the variation is not excessively increased. As a result, it is easy to maintain suitable light distribution and the uniformity of illumination light. In a case in which fd is set so as not to be equal to or higher than the upper limit of Conditional Expression (4), a convergence point of luminous flux close to the optical axis Z can be made to be present inside the illumination lens L1 even though there is a variation caused by manufacturing tolerance. Accordingly, it is possible to improve robustness in changing light to low-invasive light. Further, since diffracted light caused by scratches can be relatively suppressed even though scratches or the like are present on the emission surface S2, the unevenness of illumination light can be reduced. In a case in which the illumination lens L1 is formed so as to satisfy the following Conditional Expression (4-1) instead of the Conditional Expression (4), better characteristics can be obtained.

$$0.1 < fd/t < 1 \tag{4}$$

$$0.15 < fd/t < 0.95 \tag{4-1}$$

Further, as shown in FIG. 1, a distance between the surface apex of the incident surface S1 and an intersection of the extension line of refracted light of a ray from the incident surface S1 and the optical axis Z in the direction of the optical axis, in a case in which the ray is incident on the incident surface S1 in parallel to the optical axis at a height of 0.4×hmax, is denoted by D4; a distance between the surface apex of the incident surface S1 and an intersection of the extension line of refracted light of a ray from the incident surface S1 and the optical axis Z in the direction of the optical axis, in a case in which the ray is incident on the incident surface S1 in parallel to the optical axis Z at a height of 0.8×hmax, is denoted by D8; and the maximum height of the aspherical surface of the incident surface S1 from the optical axis Z is denoted by hmax. In this case, it is preferable that the illumination lens L1 is formed so as to satisfy the following Conditional Expression (5). In a case in which hmax is set so as not to be equal to or lower than the lower limit of the Conditional Expression (5), it is easy to make the convergence point of luminous flux be present inside the illumination lens L1 even though there is a variation caused by manufacturing tolerance. Accordingly, it is possible to improve robustness in changing light to low-invasive light. Further, since diffracted light caused by scratches can be relatively suppressed even though scratches or the like are present on the emission surface S2, the unevenness of illumination light can be reduced. In a case in which hmax is set so as not to be equal to or higher than the upper limit of Conditional Expression (5), a difference between a force for refracting a ray near the optical axis and a force for refracting a ray in the peripheral portion of the lens is not excessively large. Accordingly, the illumination lens does not needs to be formed in a shape where the gradient of the lens surface changes suddenly, and an influence of a variation is not excessively increased even though there is a variation caused by manufacturing tolerance. As a result, it is easy to maintain suitable light distribution and the uniformity of illumination light. In a case in which the illumination lens L1 is formed so as to satisfy the following Conditional Expression (5-1), better characteristics can be obtained.

$$1.8 < (D4-D8)/hmax < 2.5 \tag{5}$$

$$1.85 < (D4-D8)/hmax < 2.45 \tag{5-1}$$

It can be considered that "the extension line of refracted light" used in the definition of the D4 and D8 is the same as "the extension line of refracted light" used in the definition of fd.

Since the above-mentioned suitable structure and/or possible structures can be randomly combined, it is preferable that the above-mentioned suitable structure and/or possible structures are appropriately selectively employed according to specifications to be required. According to this embodiment, it is possible to realize an illumination lens that has wide-angle light distribution characteristics in which the quantity of light is secured even in the peripheral portion of an illumination field, is less changed depending on a wavelength, and can obtain low-invasive illumination light.

Next, numerical examples of the illumination lens of the invention will be described.

Example 1

FIG. 2 shows the structure of an illumination lens L1 of Example 1 and optical paths in a case in which rays parallel to the optical axis Z are incident on the lens. A left side in the plane of FIG. 2 is a light source side, and a right side in the plane of FIG. 2 is an object side.

The basic lens data of the illumination lens L1 of Example 1 is shown in Table 1, and aspherical coefficients are shown in Table 2. In Table 1, the surface number of the incident surface S1 is set to 1, the surface number of the emission surface S2 is set to 2, the radii of curvature of the respective surfaces are written in the column of the radius of curvature, and an interval between the incident surface S1 and the emission surface S2 on the optical axis, that is, the thickness of the lens along the optical axis is written in the column of surface spacing. Further, the refractive index of the illumination lens L1 with respect to a line d (a wavelength of 587.6 nm (nanometer)) is written in the column of Nd, and Abbe's number of the illumination lens L1 based on the line d is written in the column of Dd. Here, the sign of the radius of curvature is positive in a case in which the shape of a surface is convex toward the light source side, and is negative in a case in which the shape of a surface is convex toward the object side. The illumination lens L1 has a rotationally symmetrical structure of which the rotation axis is the optical axis Z. The diameter of the aspherical surface of the incident surface S1 and the diameter of the flat surface of the emission surface S2 are written in the column of a diameter.

In Table 1, a mark * is given to the surface number of an aspherical surface and the numerical value of a paraxial radius of curvature is written in the column of the radius of curvature of an aspherical surface. Table 2 shows the surface numbers of aspherical surfaces of Example 1 and aspherical coefficients corresponding to the respective aspherical surfaces. "E±n" (n: integer) of the numerical value of the aspherical coefficient of Table 2 means "×10$^{±n}$". The aspherical coefficients are values of the respective coefficients KA, Am (m=3, 4, 5, . . . , 20) of an aspheric equation that is expressed by the following equation.

$$Zd = C \times h^2 / \{1 + (1 - KA \times C^2 \times h^2)^{1/2}\} + \Sigma Am \times h^m$$

Zd: the depth of an aspherical surface (the length of a perpendicular extending to a plane, which meets the apex of the aspherical surface and is perpendicular to the optical axis, from a point on the aspherical surface having a height h)

h: height (a distance between the optical axis and the surface of the lens)
C: paraxial curvature
KA, Am: aspherical coefficient
Σ of the aspheric equation means the sum in regard to m.

mm (millimeter) is used as the unit of a length in the data of Table 1, but other appropriate units can also be used since an optical system can be used even though being proportionally increased or reduced in size. Further, numerical values, which are rounded off to a predetermined place, are written in each Table to be described below.

TABLE 1

Example 1

| Surface Number | Radius of Curvature | Surface Spacing | Nd | υd | Diameter |
|---|---|---|---|---|---|
| *1 | 15.0337 | 1.7800 | 1.88660 | 34.95 | 1.65 |
| 2 | ∞ | | | | 1.70 |

TABLE 2

Example 1

| Surface Number | 1 |
|---|---|
| KA | 3.0263981E+02 |
| A3 | −7.3567802E+00 |
| A4 | 1.2239105E+02 |
| A5 | −9.9168725E+02 |
| A6 | 6.8659775E+03 |
| A7 | −3.3897311E+04 |
| A8 | 1.1131365E+05 |
| A9 | −2.3577473E+05 |
| A10 | 2.7590184E+05 |
| A11 | −4.7378413E+04 |
| A12 | −1.7766259E+05 |
| A13 | −4.3056611E+05 |
| A14 | 1.6800824E+06 |
| A15 | −1.6077785E+06 |
| A16 | −2.8166879E+05 |
| A17 | 1.4335819E+06 |
| A18 | −6.8373363E+05 |
| A19 | −1.3177612E+05 |
| A20 | 1.2344129E+05 |

Since the symbol, the meaning, and the description method of each data mentioned in the description of Example 1 are the same as those of examples to be described later unless specifically noted, the repeated description thereof will be omitted below.

Example 2

Figure 4:
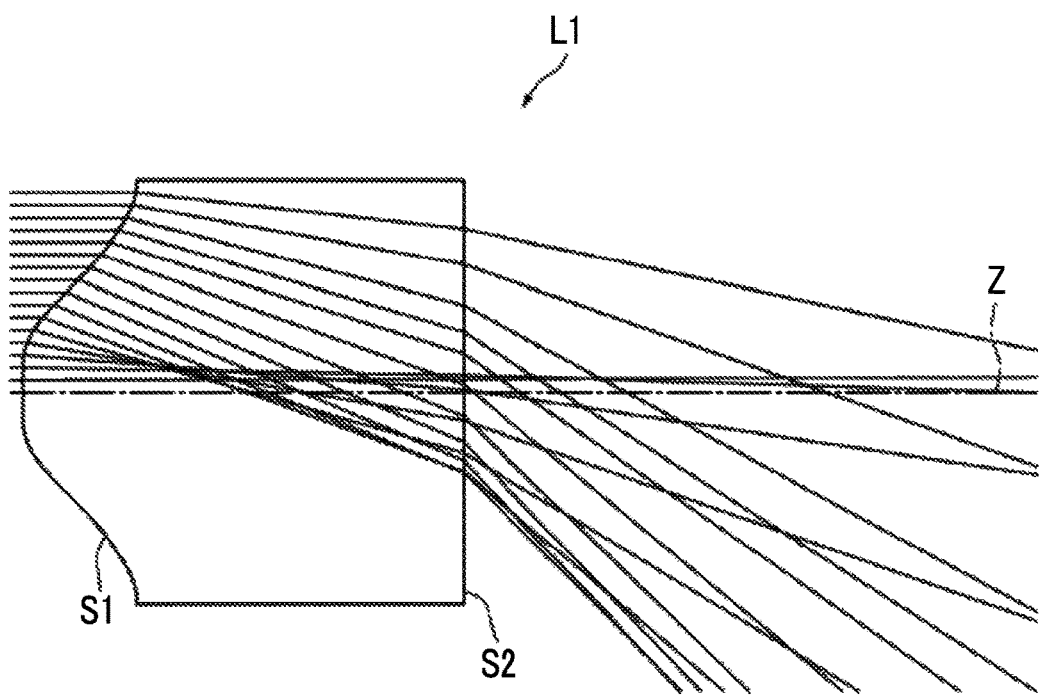
FIG. 4 is a cross-sectional view showing the structure of an illumination lens of Example 2 of the invention and optical paths.

FIG. 4 shows a cross-sectional view showing the structure of an illumination lens L1 of Example 2 and optical paths in a case in which rays parallel to the optical axis Z are incident on the lens. The basic lens data of the illumination lens L1 of Example 2 is shown in Table 3, and aspherical coefficients are shown in Table 4.

TABLE 3

Example 2

| Surface Number | Radius of Curvature | Surface Spacing | Nd | υd | Diameter |
|---|---|---|---|---|---|
| *1 | 5.0421 | 1.7800 | 1.88660 | 34.95 | 1.65 |
| 2 | ∞ | | | | 1.70 |

TABLE 4

Example 2

| Surface Number | 1 |
|---|---|
| KA | 7.2447424E−03 |
| A3 | −6.4869473E+00 |
| A4 | 1.0611902E+02 |
| A5 | −8.7382062E+02 |
| A6 | 6.3098253E+03 |
| A7 | −3.1968151E+04 |
| A8 | 1.0623395E+05 |
| A9 | −2.2620685E+05 |
| A10 | 2.6562136E+05 |
| A11 | −4.6030219E+04 |
| A12 | −1.7415232E+05 |
| A13 | −4.0444507E+05 |
| A14 | 1.6070657E+06 |
| A15 | −1.5465768E+06 |
| A16 | −2.6568039E+05 |
| A17 | 1.3734391E+06 |
| A18 | −6.5052359E+05 |
| A19 | −1.3293905E+05 |
| A20 | 1.2069743E+05 |

Example 3

Figure 5:
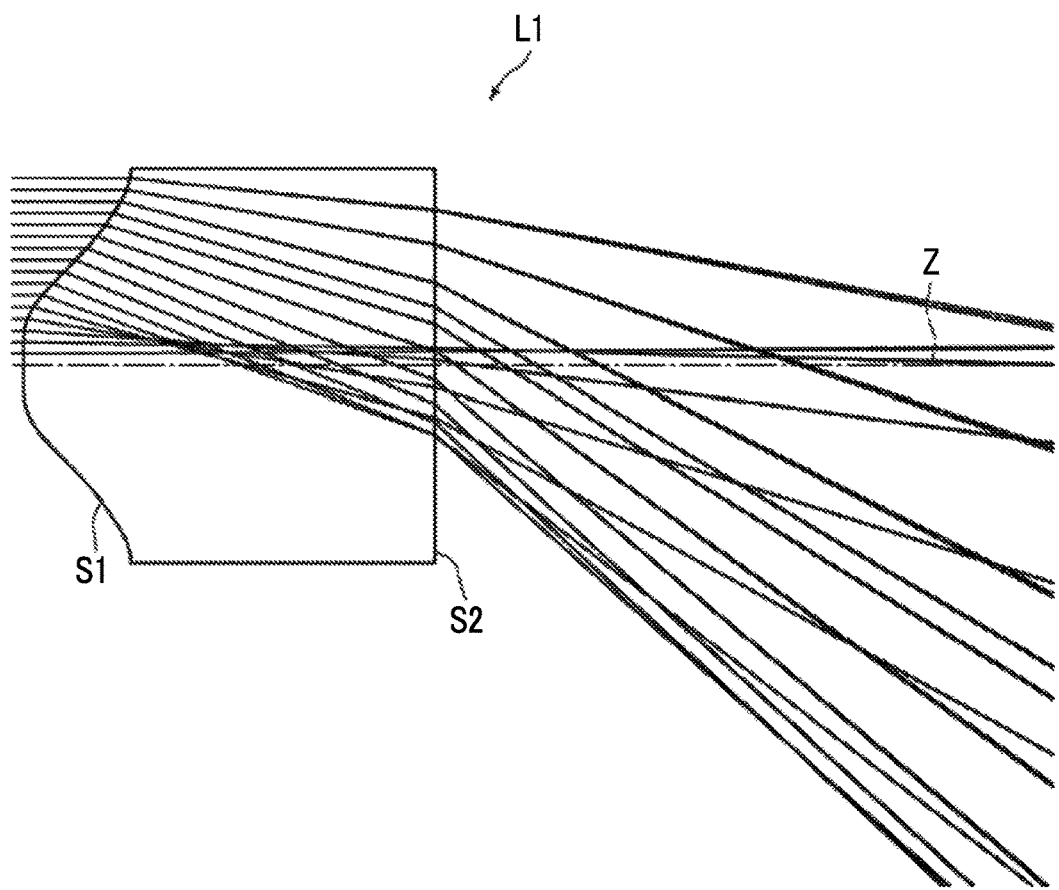
FIG. 5 is a cross-sectional view showing the structure of an illumination lens of Example 3 of the invention and optical paths.

FIG. 5 shows a cross-sectional view showing the structure of an illumination lens L1 of Example 3 and optical paths in a case in which rays parallel to the optical axis Z are incident on the lens. The basic lens data of the illumination lens L1 of Example 3 is shown in Table 5, and aspherical coefficients are shown in Table 6.

TABLE 5

Example 3

| Surface Number | Radius of Curvature | Surface Spacing | Nd | υd | Diameter |
|---|---|---|---|---|---|
| *1 | 15.5819 | 1.7800 | 1.80610 | 40.73 | 1.65 |
| 2 | ∞ | | | | 1.68 |

TABLE 6

Example 3

| Surface Number | 1 |
|---|---|
| KA | 3.0279037E+02 |
| A3 | −7.9655073E+00 |
| A4 | 1.4844342E+02 |
| A5 | −1.1638471E+03 |
| A6 | 6.0764126E+03 |
| A7 | −1.9347814E+04 |
| A8 | 3.4719715E+04 |
| A9 | −2.9293587E+04 |
| A10 | −1.3220912E+04 |
| A11 | 9.0411148E+04 |
| A12 | −9.9003669E+04 |
| A13 | −2.4635126E+05 |
| A14 | 7.7832839E+05 |
| A15 | −4.7835135E+05 |

TABLE 6-continued

Example 3

| Surface Number | 1 |
|---|---|
| A16 | −6.0774586E+05 |
| A17 | 6.9611314E+05 |
| A18 | 3.5314714E+05 |
| A19 | −7.2201131E+05 |
| A20 | 2.5767446E+05 |

Table 7 shows corresponding values of Conditional Expressions (1) to (5) with regard to the illumination lenses L1 of Examples 1 to 3. The corresponding values of Conditional Expression (4) of Table 7 are values in a case in which rays parallel to the optical axis at a height of 0.36× hmax are incident on the incident surface S1 in all of Examples 1 to 3. A line d is used as a reference wavelength in Examples 1 to 3, and values shown in Table 7 are values based on the reference wavelength.

TABLE 7

| Expression Number | | Example 1 | Example 2 | Example 3 |
|---|---|---|---|---|
| (1) | hs/hmax | 0.46 | 0.48 | 0.45 |
| (2) | Nd | 1.8866 | 1.8866 | 1.80610 |
| (3) | νd | 34.95 | 34.95 | 40.73 |
| (4) | fd/t | 0.46 | 0.46 | 0.48 |
| (5) | (D4 − D8)/hmax | 2.02 | 2.09 | 2.09 |

Figure 6:
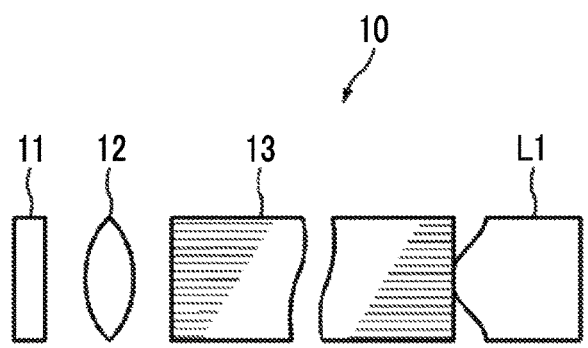
FIG. 6 is a diagram showing the schematic structure of an illumination optical system for an endoscope according to an embodiment of the invention.

Next, an illumination optical system 10 for an endoscope according to an embodiment of the invention will be described. FIG. 6 is a diagram showing the schematic structure of the illumination optical system 10 for an endoscope according to the embodiment of the invention. The illumination optical system 10 for an endoscope includes a light source 11, an optical coupling lens 12, a light guide member 13, and the illumination lens L1 according to the embodiment of the invention. For example, a light emitting diode (LED) or a laser can be used as the light source 11. The optical coupling lens 12 is a lens that optically couples the light source 11 to the light guide member 13. The light guide member 13 is to guide light, which is generated from the light source 11, to the illumination lens L1. For example, a light guide formed of a fiber bundle can be used as the light guide member 13. Since the illumination optical system 10 for an endoscope includes the illumination lens L1 according to the embodiment of the invention, the illumination optical system 10 for an endoscope has wide-angle light distribution characteristics in which the quantity of light is secured even in the peripheral portion of an illumination field, is less changed depending on a wavelength, and can obtain low-invasive illumination light.

The invention has been described above using embodiments and examples, but is not limited to the embodiments and examples and may have various modifications. For example, the radius of curvature, the surface spacing, the refractive index, Abbe's number, and the aspherical coefficient of each lens are not limited to the values mentioned in each numerical example, and may take other values. Further, the illumination lens of the invention can also be applied to an illumination optical system other than the illumination optical system for an endoscope.

What is claimed is:

1. An illumination lens that is used in an illumination optical system for an endoscope, the illumination lens consisting of:
   one lens,
   wherein an aspherical surface is formed on an incident surface on which light generated from a light source is to be incident so that the incident surface has a convex shape in a paraxial region,
   the aspherical surface has at least one hs satisfying Conditional Expression (1) expressed by "0<hs/hmax<0.5 (1)" in a case in which a height from an optical axis is denoted by h, the amount of sag at each point on the aspherical surface corresponding to the height h is expressed by Sag(h) as a function of h, a height at which a second derivative of Sag(h) with respect to h is 0 is denoted by hs, and a maximum height of the aspherical surface from the optical axis is denoted by hmax, and
   Conditional Expression (2) expressed by "1.79<Nd<2 (2)" is satisfied in a case in which a refractive index of the illumination lens with respect to a line d is denoted by Nd.

2. The illumination lens according to claim 1,
   wherein Conditional Expression (3) expressed by "34.5<νd<47.5 (3)" is satisfied in a case in which Abbe's number of the illumination lens based on the line d is denoted by Dd.

3. The illumination lens according to claim 2,
   wherein Conditional Expression (3-1) expressed by "34.75<νd<47.25 (3-1)" is satisfied.

4. The illumination lens according to claim 1,
   wherein an emission surface from which the light incident from the incident surface is to be emitted is a flat surface.

5. The illumination lens according to claim 1,
   wherein an intersection of a ray incident on the incident surface in parallel to the optical axis at a height of 0.1×hmax and a ray incident on the incident surface in parallel to the optical axis at a height of 0.4×hmax is positioned inside the illumination lens.

6. The illumination lens according to claim 5,
   wherein the intersection is positioned closer to the light source than a middle point of a thickness of the illumination lens, which is positioned on the optical axis, in a direction of the optical axis.

7. The illumination lens according to claim 1,
   wherein in a case in which a distance between an intersection of a ray incident on the incident surface in parallel to the optical axis and the incident surface and an intersection of an extension line of refracted light of the ray from the incident surface and the optical axis in a direction of the optical axis is denoted by fd and a thickness of the illumination lens along the optical axis is denoted by t, at least a part of rays, which are incident on the incident surface in parallel to the optical axis at a height ha in a range of "0.1×hmax≤ha≤0.5×hmax", satisfy Conditional Expression (4) expressed by "0.1<fd/t<1 (4)".

8. The illumination lens according to claim 7,
   wherein at least a part of rays, which are incident on the incident surface in parallel to the optical axis at a height ha in a range of "0.1×hmax≤ha≤0.5×hmax", satisfy Conditional Expression (4-1) expressed by "0.15<fd/t<0.95 (4-1)".

9. The illumination lens according to claim 1,
   wherein Conditional Expression (5) expressed by "1.8< (D4−D8)/hmax<2.5 (5)" is satisfied in a case in which a distance between an surface apex of the incident surface and an intersection of an extension line of refracted light of a ray from the incident surface and the optical axis in the direction of the optical axis, in a case in which the ray is incident on the incident surface in parallel to the optical axis at a height of 0.4×hmax, is denoted by D4 and a distance between the surface apex of the incident surface and an intersection of an extension line of refracted light of a ray from the incident surface and the optical axis in the direction of the optical axis, in a case in which the ray is incident on the incident surface in parallel to the optical axis at a height of 0.8×hmax, is denoted by D8.

10. The illumination lens according to claim 9,
wherein Conditional Expression (5-1) expressed by "1.85<(D4−D8)/hmax<2.45 (5-1)" is satisfied.

11. The illumination lens according to claim 1,
wherein the aspherical surface has only one hs in a range of "0<h≤hmax" in a cross section including the optical axis.

12. The illumination lens according to claim 1,
wherein the aspherical surface has at least one hs satisfying Conditional Expression (1-1) expressed by "0<hs/hmax<0.49 (1-1)".

13. The illumination lens according to claim 1,
wherein Conditional Expression (2-1) expressed by "1.8<Nd<2 (2-1)" is satisfied.

14. An illumination optical system for an endoscope comprising:
the illumination lens according to claim 1.

* * * * *